United States Patent [19]
Mazurek et al.

[11] Patent Number: 6,146,590
[45] Date of Patent: *Nov. 14, 2000

[54] VESSEL FOR AN ANALYTIC TEST DEVICE

[75] Inventors: Martha Mazurek, Ann Arbor; Janet Shantz, Belmont; Matt Hansen, Rockford, all of Mich.

[73] Assignee: Mainline Technology, Inc., Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 09/107,562

[22] Filed: Jun. 29, 1998

[51] Int. Cl.⁷ .................................................. G01N 33/48
[52] U.S. Cl. .............................................. 422/58; 422/61
[58] Field of Search ................................... 422/58, 56–61

[56] References Cited

U.S. PATENT DOCUMENTS 4,635,488  1/1987  Kremer ........................... 422/59
5,504,013  4/1996  Senior ............................. 436/165
5,622,871  4/1997  May et al. .
5,658,531  8/1997  Cope et al. ........................ 422/58

*Primary Examiner*—Lyle A. Alexander
*Attorney, Agent, or Firm*—Young & Basile, P.C.

[57] ABSTRACT

A vessel for an analytic test device of the type including a sample receiving member and one or more other components for conducting an analytical test is disclosed. The vessel comprises a body portion having an interior volume for holding the components for the analytical test, including the sample receiving member. The body portion includes a first opening for communicating a sample to be tested into the body portion, and a second opening to permit visual confirmation of the results of the analytical test. A single cover portion is mateable with the body portion to cover the first opening, the cover portion being further alternatively mateable with the body portion away from the first opening so that the second is still visible.

13 Claims, 2 Drawing Sheets

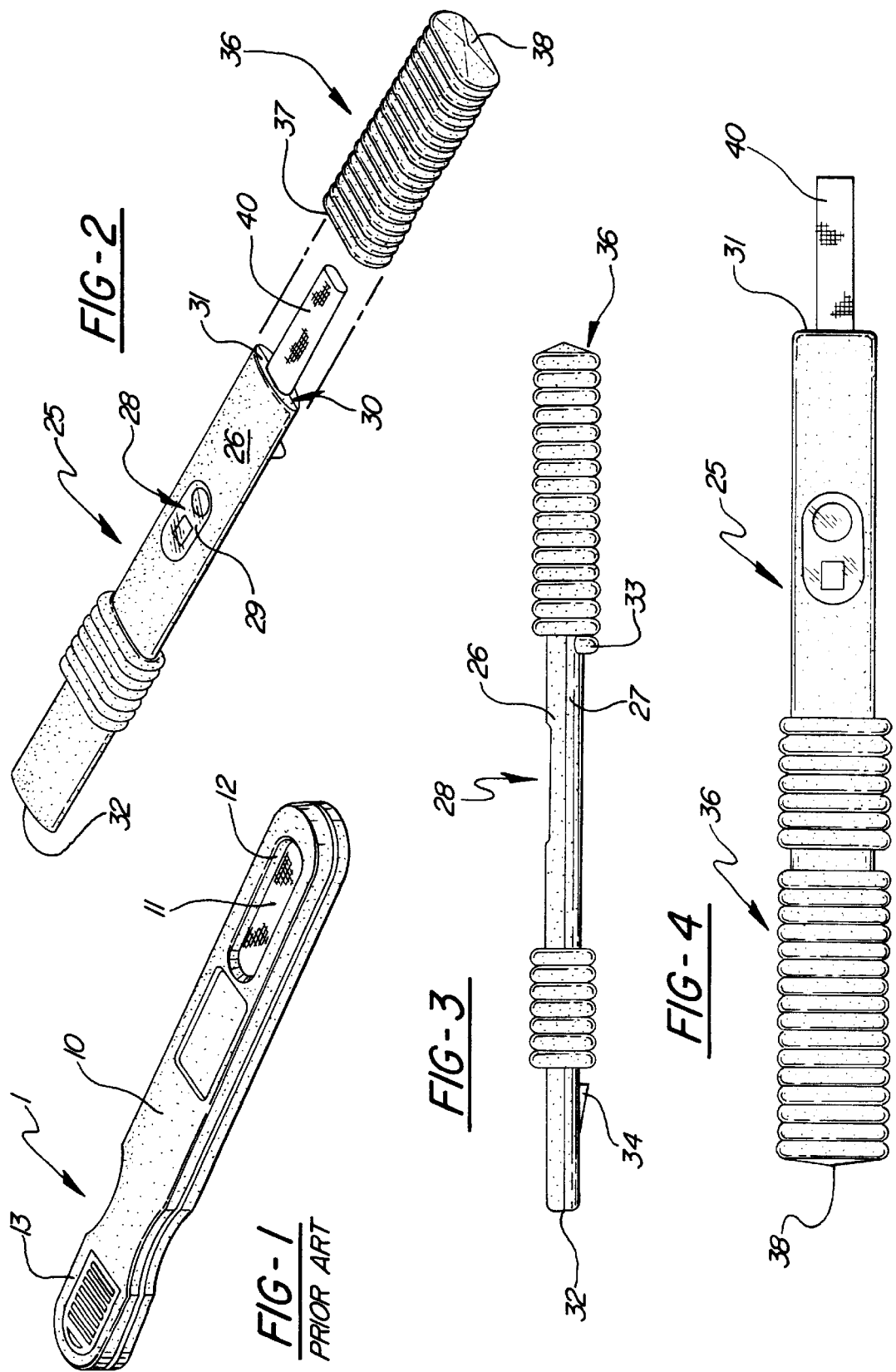

VESSEL FOR AN ANALYTIC TEST DEVICE

FIELD OF THE INVENTION

The present invention relates to a vessel for an analytic test device, for example a pregnancy or ovulation test device, and more particularly to such a vessel having a body portion including an opening for a sample receiving member, and a cover portion mateable with the body portion proximate the opening to define a cover for the sample receiving member, the cover portion being further alternatively mateable with the body portion distal from the opening to extend the distance between the sample receiving member and the hand of a person holding the vessel.

BACKGROUND OF THE INVENTION

Analytic test devices, such as for use in home pregnancy and ovulation tests, are commercially available and widely used. Home pregnancy and ovulation test devices in particular are typified by ease of use, simply requiring one time contact with an appropriate biological sample, such as the urine stream. Analysis of the biological sample is self-contained and automatic; results typically being observable in a matter of minutes after contact with the biological sample.

An exemplary prior art test device generally designated 1, and having application as a pregnancy test device, is shown in FIG. 1. The device comprises a unitary vessel 10 housing an absorbent biological sample receiving member 11, which sample receiving member is exposed through an opening 12 provided through the upper surface of vessel 10. Sample receiving member 11 communicates with an analytic test strip (not shown) disposed within vessel 10, the test strip containing or communicating with one or more test specific reagents. An end 13 of vessel 10 spaced apart from opening 12 is provided for grasping of the test device 1 by a user, particularly when obtaining a biological sample. A window (not shown) provided through the opposite, lower surface of vessel 10 reveals a portion of the analytic test strip to permit viewing of the test results.

Unfortunately, the mean distance between opening 12 and end 13 in the prior art test device, approximately 120 millimeters in the illustrated device 1, is such as to make obtaining a biological sample a difficult and clumsy procedure, particularly in the case of pregnancy and ovulation tests where the user is required to urinate on the sample receiving member. A too frequent result in such tests is unwanted contact between the user's hand and the biological sample.

Accordingly, it is an object of the present invention to provide a vessel for an analytic test device, for example a pregnancy or ovulation test device, according to which a user may conveniently and easily obtain a suitable sample, such as a biological sample, while avoiding any unwanted contact therewith.

Still another object of the present invention is to provide a vessel for an analytic test device that is inexpensive of both cost and manufacture, and simple in operation.

These and other objects and advantages of the present invention are accomplished via a vessel for an analytic test device wherein the vessel comprises a body portion including an opening for a sample receiving member, and a cover portion mateable with the body portion proximate the opening to define a cover for the sample receiving member. The body portion defines a first length; the cover portion being further alternatively mateable with the body portion distal from the opening to define in combination a second length greater than the first length of the body portion.

According to a further feature of the present invention, the body portion is characterized by a generally rectangular shape including first and second ends defining the first length of the body portion therebetween. According to this feature, the opening for the sample receiving member may be provided proximate the first end of the body portion.

According to another feature of this invention, the first length of the body portion is approximately 119 millimeters, while the second length is approximately 150 millimeters.

At least one tab element is also provided on the body portion, the cover portion being receivable over the at least one tab element to securely removably mate the cover portion to the body portion. The at least one tab element is, according to one feature of this invention, provided proximate the second end of the body portion.

According to still a further inventive feature, at least one riser is provided for maintaining the body portion above a support surface. The riser may be provided proximate the opening, so as to maintain the sample receiving member above a support surface, particularly during test development.

BRIEF DESCRIPTION OF THE DRAWINGS

FIG. 1 comprises a quartering perspective view of a prior art analytic test device;

FIG. 2 comprises a quartering perspective view of the present inventive vessel showing the cover and body portions thereof in a separated condition;

FIG. 3 comprises a lateral elevational view of the present inventive vessel showing the cover portion thereof secured over a first end of the body portion;

FIG. 4 comprises a top elevational view of the present inventive vessel showing the cover portion thereof secured over a second end of the body portion distal from the opening for the sample receiving member.

DESCRIPTION OF THE ILLUSTRATED EMBODIMENT

Figure 5:
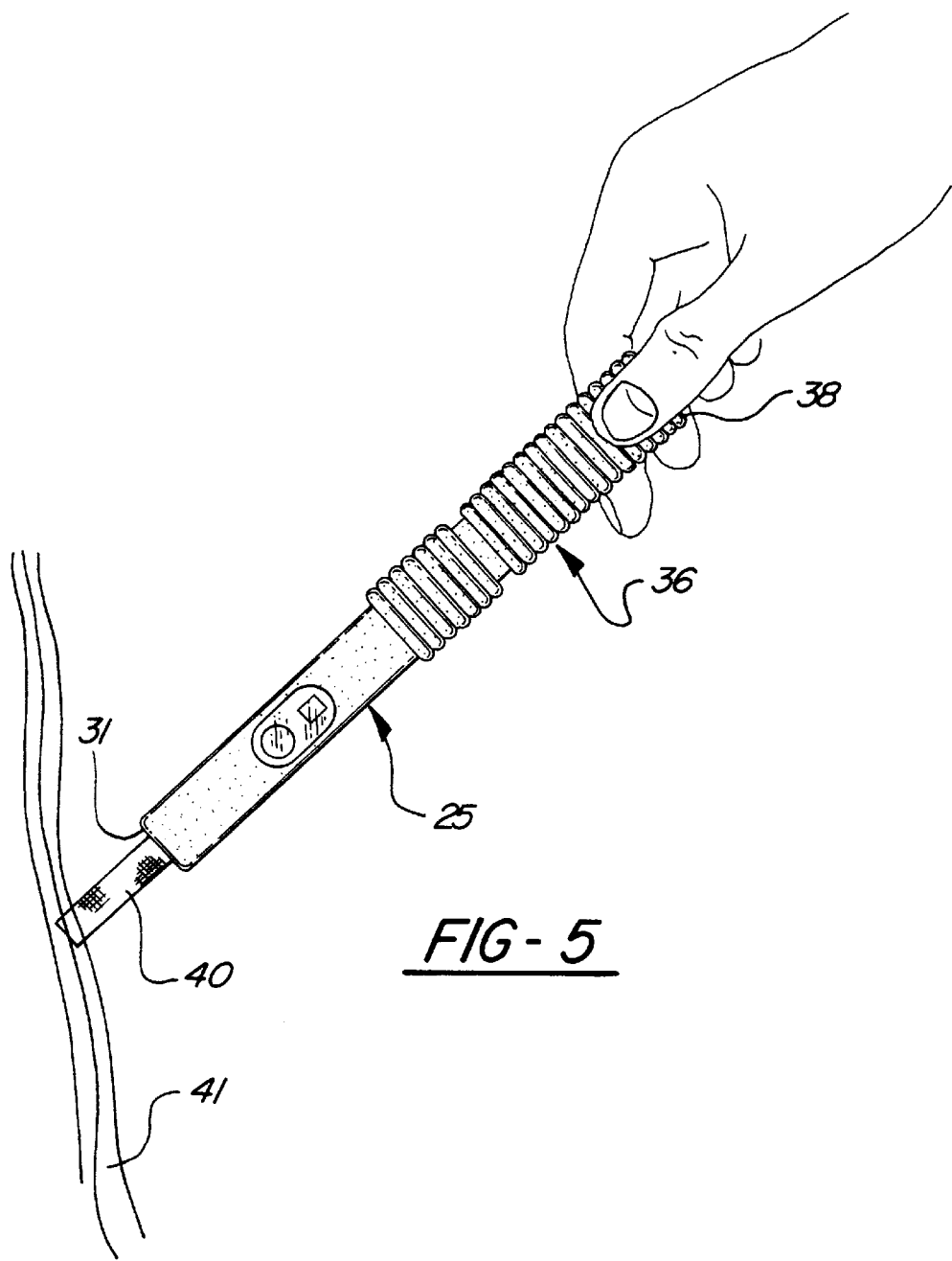
FIG. 5 depicts the present inventive vessel in application as a pregnancy or ovulation test device.

With reference now to the drawings, the individual elements of the present inventive vessel and their interrelation will be better understood. And while the present invention is exemplified as a vessel for a pregnancy or ovulation analytic test device, it will be appreciated by those of skill in the art that such application is not meant to be limiting of the present invention, which is suitable as a vessel for numerous analytic test devices, both in biological and other applications.

As shown in FIGS. 2 and 3, the vessel of the present invention generally comprises mateable body 25 and cover 36 portions. In the illustrated embodiment, body portion 25 defines an elongate, generally flat, rectangular body comprising upper 26 and lower 27 halves. The distance between first 31 and second 32 ends of body portion 25 defines a preferred first length of approximately 119 millimeters. Upper 26 and lower 27 halves are longitudinally mateable to define a unitary housing for the selected analytic components, and may be secured together during assembly by known means. One or more viewing windows 28 are provided through upper half 26 of body portion 25 to permit visual confirmation of test results. A transparent cover 29 (not shown in FIG. 3), preferably fabricated from a suitable polymer, is secured, such as by a suitable adhesive, to body portion 25 over viewing window 28 to prevent unwanted contamination of the test strip or other analytic components by the sample or other substance.

An opening 30 is provided for a sample receiving member 40 comprising an absorbent wick. According to the illustrated embodiment, opening 30 is provided in a first 31 end of body portion 25 and sample receiving member 40 extends therefrom away from the body portion as shown. Of course, it will be appreciated that opening may be provided elsewhere through body portion 25, such as through an upper surface thereof as taught in the prior art test device of FIG. 1.

Sample receiving member 40 contacts a test strip (not shown) provided within body portion 25 to communicate a sample thereto. The test strip includes or communicates with one or more test-specific binding reagents, as is well-known to those of skill in the art, for performing the desired analysis of the sample. As will be understood from the remainder of this disclosure, the foregoing analytic components, including the sample receiving member 40, test strip, and binding reagents, are shown to exemplify an application of the present invention and comprise no part thereof, but may instead be selected according to individual requirements, such as the type of analysis being performed.

At least one riser 33 depending vertically from lower half 27 of body portion 25 as shown is provided for elevating at least the first end 31 thereof, and, consequently, the sample receiving member 40, above a support surface (not shown), particularly during test development. Because it is desirable in at least some applications to maintain the test vessel in a horizontal attitude during test development, at least a second riser (not shown) or, as depicted, at least a portion of cover 36 and/or body 25 is provided having radial dimensions comparable to riser 33. In the invention as shown, the position of riser 33 along the longitudinal axis of body portion 25 is such that the riser also serves as a stop surface against over-insertion of first end 31 of the body portion into cover portion 36.

Cover portion 36 is preferably approximately 55 millimeters in overall length between opposite first 37 and second 38 ends thereof. According to the present invention, cover portion 36 includes an interior blind bore (not shown) opening towards first end 37 thereof and dimensioned to alternatively mateably receive both first 31 and second 32 ends of body portion 25 therein. When mated with first end 31 of body portion 25, cover portion 36 defines a cover for sample receiving member 40 exposed through opening 30. To this end, bore is, in the illustrated embodiment, preferably of sufficient internal dimensions to completely cover the exposed portion of sample receiving member 40. A ramped tab 34 protruding from lower 27 half of body portion 25 proximate second end 32 is receivable within cover portion 36 and serves to urge the cover and body portions into secure frictional engagement. A further such tab (not shown) may also be provided proximate first end 31 as desired.

Body 25 and cover 36 portions are preferably manufactured from a material suitably impervious to the appropriate sample (e.g., urine), except through conveyance by the sample receiving member 40. In the illustrated embodiment, body 25 and cover 36 portions are fabricated from polymer. Of course, both material and construction (i.e., upper 26 and lower 27 longitudinally mateable halves) of the present inventive vessel may be varied according to individual preference and the requirements of the particular analytic test, such considerations not constituting part of the present invention.

In operation of the present inventive test vessel, depicted in FIGS. 4 and 5, cover portion 36 is removed from first end 31 to expose sample receiving member 40, the cover portion being subsequently mated with second end 32 (not visible) and urged onto tab 34 (not shown) to securely removably mate cover portion 36 to body portion 25. In this latter configuration, with cover portion 36 and body portion 25 thus combined, the vessel defines a second length between first end 31 of body portion 25 and second end 38 of cover portion 36, which second length is greater than the first length of body portion 25 previously described (i.e., the distance between first 31 and second 32 ends). This second length is preferably approximately 150 millimeters. With cover portion 36 thus mated to body portion 25, the length of the vessel is extended so that a user can grasp cover portion 36 and dispose the sample receiving member 40 in the appropriate sample 41 (e.g., a urine stream) at a greater distance from the user's hand, thereby reducing the likelihood that the user's hand will inadvertently contact the sample.

It will of course be appreciated that the foregoing is merely illustrative of one embodiment of the present invention, and that additional modifications and improvements, apparent to those of skill in the art, are certainly possible without departing from the spirit and broader aspects this invention as set forth in the appended claims.

What is claimed is:

1. A vessel for an analytic test device of the type including a sample receiving member and one or more other components for conducting an analytical test, said vessel comprising:

a body portion defining a housing for said components for the analytical test, including the sample receiving member, said body portion including a first opening for conveying a sample to be tested to the sample receiving member, a second opening to permit visual confirmation of the results of the analytical test, and said body portion defining a first length; and a cover portion mateable with said body portion proximate said opening to define a cover for the sample receiving member, said cover portion further alternatively mateable with said body portion distal from said first opening such that a majority of said cover portion extends beyond said body portion to thereby define in combination a second length greater than said first length of said body portion, wherein further, when said cover portion is mated with said body portion distal from said first opening, said cover portion does not cover said second opening.

2. The vessel of claim 1, wherein said body portion is characterized by a generally rectangular shape including first and second ends defining said first length of said body portion therebetween.

3. The vessel of claim 2, wherein said opening is provided proximate said first end of said body portion.

4. The vessel of claim 1, wherein said body portion includes at least one tab element, said cover portion receivable over said at least one tab element.

5. The vessel of claim 4, wherein said body portion includes first and second ends, and said at least one tab element is provided proximate said second end of said body portion.

6. The vessel of claim 1, further including at least one riser for maintaining said body portion above a support surface.

7. The vessel of claim 6, wherein said at least one riser is provided proximate said opening.

8. A vessel for an analytic test device of the type including a sample receiving member and one or more other components for conducting an analytical test, said vessel comprising:

a body portion defining a housing for the sample receiving member and the one or more other components for the analytical test, said body portion having first and second ends, and further including a first opening proximate said first end for the sample receiving member to project therethrough, and a second opening to permit visual confirmation of the results of the analytical test;

a cover portion mateable with said first end of said body portion to define a cover for the sample receiving member, said cover portion further alternatively mateable with said second end of said body portion such that said cover portion extends beyond said second end of said body portion to define a handle for grasping said vessel; and wherein, when said cover portion is mated with said second end of said body portion said cover portion does not cover said second opening.

9. The vessel of claim 8, wherein said body portion further includes at least one tab element, said cover portion receivable over said at least one tab element.

10. The vessel of claim 9, further including at least one riser projecting a sufficient distance from said body portion so as to maintain at least said first end of said body portion at a distance above a support surface.

11. A vessel for an analytic test device of the type including a sample receiving member and one or more other components for conducting an analytical test, said vessel comprising:

a body portion having an interior volume for holding the components for the analytical test, including the sample receiving member, said body portion including a first opening for communicating a sample to be tested into said body portion, and a second opening to permit visual confirmation of the results of the analytical test; and a single cover portion mateable with said body portion to cover said first opening, said cover portion further alternatively mateable with said body portion away from said first opening; and wherein when said cover portion is mated with said body portion away from said first opening, said second opening is still visible.

12. The vessel of claim 11, wherein said body portion and said cover are mateable in an interference fit relationship.

13. The vessel of claim 11, wherein said body portion includes at least one riser for maintaining at least said first opening of said body portion at a distance above a support surface.

* * * * *

UNITED STATES PATENT AND TRADEMARK OFFICE
CERTIFICATE OF CORRECTION

PATENT NO : 6,146,590
DATED : November 14, 2000
INVENTOR(S): Martha Mazurek et al It is certified that error appears in the above-identified patent and that said Letters Patent are hereby corrected as shown below:

On the title page:
In the Abstract, last line, after "second", insert --opening--.

Signed and Sealed this

First Day of May, 2001

Attest:

NICHOLAS P. GODICI

Attesting Officer

Acting Director of the United States Patent and Trademark Office